Figure 1A:
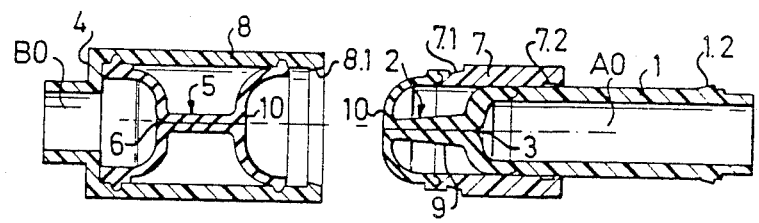

United States Patent [19]
Albinsson

[11] Patent Number: 4,804,015
[45] Date of Patent: Feb. 14, 1989

[54] CONNECTION DEVICE AVOIDING CONTAMINATION

[75] Inventor: Carl G. U. Albinsson, Mölndal, Sweden

[73] Assignee: Steridose Systems AB, Askim, Sweden

[21] Appl. No.: 942,166

[22] Filed: Dec. 16, 1986

[30] Foreign Application Priority Data

Dec. 20, 1985 [SE] Sweden .................... 8506074

[51] Int. Cl.⁴ .................................... F16L 29/00
[52] U.S. Cl. ....................... 137/614.03; 251/342; 251/901
[58] Field of Search ........ 137/614, 614.01, 614.02, 137/614.03, 614.05; 251/149, 149.8, 341, 342, 347, 901

[56] References Cited

U.S. PATENT DOCUMENTS

| | | | |
|---|---|---|---|
| 2,755,060 | 7/1956 | Twyman | 251/342 |
| 2,958,545 | 11/1960 | Stelzer | |
| 3,084,693 | 4/1963 | Cathcart | |
| 3,690,344 | 9/1972 | Brumm | 251/901 X |
| 4,111,221 | 9/1978 | Olsen | 251/901 X |
| 4,219,221 | 8/1980 | Webb | |

FOREIGN PATENT DOCUMENTS

| | | |
|---|---|---|
| 0151371 | 5/1985 | European Pat. Off. |
| 1732271 | 4/1956 | Fed. Rep. of Germany |
| 2415007 | 10/1974 | Fed. Rep. of Germany |
| 1491652 | 11/1974 | Fed. Rep. of Germany |
| WO82/00698 | 3/1982 | PCT Int'l Appl. |
| WO84/02321 | 6/1984 | PCT Int'l Appl. |
| 74042219 | 4/1979 | Sweden |

Primary Examiner—A. Michael Chambers
Assistant Examiner—John C. Fox
Attorney, Agent, or Firm—Brumbaugh, Graves, Donohue & Raymond

[57] ABSTRACT

A connection device for connecting two spaces, comprising two connector parts (1,11) (4,14) each having a flexible tubular member (2,12) (5,15) which members have sealing surfaces (3,13) (6,15) which on connection are brought to bear on a surface belonging to the other connector part by the first tubular member being introduced into the second connector part and inverted inside out.

8 Claims, 2 Drawing Sheets

CONNECTION DEVICE AVOIDING CONTAMINATION

TECHNICAL FIELD

The present invention is related to a connection device for forming communication between two spaces avoiding contamination of a clean area from a contaminated area, which areas are the interior of said spaces and the environment, or vice versa.

In health care it is a commonly occurring problem to be able to connect conduits and vessels having sterile or aseptic contents without the contents being contaminated from the environment. This is the case on parenteral liquid administration to a patient whereby conduits and containers in an infusion system are to be connected to each other, and in many cases drugs are to be introduced into the infusion system in solid or liquid form without contaminating the liquid supplied to the patient with infectious matter or other harmful matter from the environment. There are also cases where contamination of the environment from the interior of conduits and vessels has to be avoided or mutual contamination between the interior and the environment has to be avoided, for example on handling of toxic cytostatics on infusion or on handling of possibly infected blood. Connections for ostomy bags are subject to similar problems.

In industry there are similar needs for contamination-free connection, for example when a sample is taken out of a fermentation vessel or when noxious matter is to be transported without waste.

The object of the present invention is to obtain a connection device which more securely than present connection devices permits contamination-free connection while being easy to handle.

STATE OF THE ART

In systems for parenteral liquid administration it has previously been used connecting devices with thread or bayonet catch or taper connections such as Luer, which are protected by a cap or the like which is taken off before connecting the same. The handling of these is inconvenient and the risk of contamination of parts of the connecting devices which will get into contact with a clean area can not be safely avoided.

On supply of a second liquid, for example a drug solution, into an infusion system through which a first liquid, for example a drug solution is administered, the infusion system has been provided with a port having a rubber membrane which one penetrates with a cannula connected to the source or the second liquid. Neither in this case can contamination through impurities on the membrane and/or the cannula be safely avoided, and further there is a risk that personnel is injured by the cannula on application thereof.

SE-B-407517 (corresponding to DE-B-2415007 and U.S. Pat. No. 3,865,411) shows a sterile connector for the end of a conduit, which is used in a line for blood or blood components and wherein a resilient deformable gasket is arranged around the outer end of the conduit, whereby a continuous, removable, yieldable, flexible strip material is used, a portion of which is removably adhered to the gasket and overlies the end of the conduit, said strip material having a free end, and being in generally U-shaped configuration, whereby a force applied to the free end thereof will withdraw the entire strip material to expose the end of the conduit. In other words, two tube ends provided with gaskets are connected by withdrawing two folded tape strips sideways thus that clean contact surfaces of the gaskets are exposed along a line and are pressed together by a force applied by a clamp or the like. While the thus known device enables a sterile connection there is a risk that a gap occurs between the ends of the conduits on withdrawal of the tape strips, especially if the force pressing the conduit ends together should be released by some cause. Furthermore the connecting operation requires at least two steps, namely pressing the conduit ends together and withdrawing the tape strips. Finally, it is not possible to separate the connector parts and getting back a sterile seal of either part.

DESCRIPTION OF THE INVENTION

According to the invention it is achieved a connection device of the kind mentioned initially which fulfills the objects given above and has unexpected advantages as compared with previously known technique. The invention is characterized in that the first space is in communication with a first connector part in which said first space is sealed by a first tubular member made of flexible material, said tubular member having an inner sealing surface which sealingly bears on itself or on another surface belonging to the first connector part; that the second space is in communication with a second connector part in which said second space is sealed by a second tubular member made of flexible material, said tubular member having a sealing surface which sealingly bears on itself or on another surface belonging to the second connector part; and that the first connector part is adapted to be connectable with the second connector part to formation of the communication between the two spaces in such manner that the first tubular member is introduced into the second tubular member and inverted inside out, whereby a portion of the sealing surface thereof is brought to sealingly bear on a surface belonging to the second connector part at the same time as a portion of the sealing surface belonging to the second connector part is brought to sealingly bear on a surface belonging to the first connector part, and whereby portions of the tubular members having been exposed to a contaminated area is carried away in a direction away from the clean area.

The principle of the present invention is that contaminated portions are carried away from the clean area in a radial direction, outwards or inwards depending on the configuration of the connecting device according to embodiments of the invention presented below.

A first major embodiment of the invention is characterized in that the inner sealing surface of the first tubular member has opposite portions which sealingly bear on each other; that the sealing surface of the second tubular member has opposite inside portions which sealingly bear on each other; and that on joining the connector parts portions of the sealing surfaces of the two tubular members will be brought to sealingly bear on each other. In said first embodiment preferably the first tubular member has a rigidifying wall which facilitates the introduction and inversion thereof into the second tubular member.

A second major embodiment of the invention is characterized in that the inner sealing surface of the first tubular member has opposite portions which sealingly bear on the outer surface of a rod disposed inside said tubular member, said rod being adapted to be introduceable into the second connector part, which outer surface has at least one opening into the first space; that the sealing surface of the second tubular member is an outward surface which sealingly bears on the inner surface of a cavity around the sealing tubular member, which cavity in said inner surface has at least one opening into the second space: and that on joining the connector parts the sealing surface belonging to the first connector part is brought, on introducing the rod into the connector part of the second space, to sealingly bear on the inner surface of the cavity of the second connector part at the same time as the sealing surface belonging to the second connector part is brought to sealingly bear on the outer surface of the rod, whereupon the two openings are uncovered and brought into communication with each other.

In both the first and the second major embodiments of the invention the connection device is preferably characterized in that either or both sealing surfaces are coated with adhesive material, and/or that the connection device is adapted for irreversible connection of the connector parts, or that the connection device is designed in such manner that the connection can be disconnected, whereupon the two spaces are re-sealed, and/or that the connector parts are provided with mating abutting members and/or that a membrane is arranged to cover the ends of either or both tubular members directed away from the respective spaces.

Another aspect of the invention is use of a connection device according to the invention in a device for parenteral liquid administration to a patient. Such use is in particular for forming a connection through which a drug may be introduced into the device for parenteral liquid administration.

Preferably the connector parts are rotation symmetrical along the axis thereof, whereby on connection, contaminated surface portions are carried away in a direction away from a central point or a circle, respectively, but alternatively the connecting devices may have a cross section which is elongated or otherwise non-circular whereby contaminated surface portions are carried away radially from a finite line portion or a closed curve, respectively.

The radial transport of contaminated matter from the interior of the connecting device of course goes in the opposite direction on separating the connecting device.

The invention is further described with reference to the enclosed drawings where FIG. 1 a, b, c shows a connection device according to one embodiment of the invention (a) before assembling, (b) in an assembled position and (c) in a connected position, and FIG. 2 a, b, c, d shows a connection device according to another embodiment of the invention (a) before assembling, (b) in an assembled position, (c) in an intruded position and (d) in an opened position.

The connection device shown in FIG. 1 is rotation symmetrical. With reference to FIG. 1a a first connector part 1 is tube-shaped and defines a space AO therein which is shown open at its right-hand end where space AO may continue into a first vessel of any kind. At its left-hand end part 1 has sealed thereto a flexible tubular member 2 having a proximal cylindrical part, an intermediate collapsed part wherein an inner sealing surface 3 has opposite parts which are in contact to sealingly bear on each other thus that space AO is sealed, and a distal curved part, the end of which is sealed to an outer guiding socket 7 which is slideable over and along the first connector part 1. A second connector part 4 is generally tube shaped, defining a space BO therein which may continue into a second vessel of any kind. A support socket 8 forms a section of part 4 with enlarged diameter, in which a flexible tubular member 5 is attached at its distal and proximal ends. Member 5 has an intermediate collapsed part wherein an inner sealing surface 6 has opposite parts which are in contact to sealingly bear on each other thus that space BO is sealed. Complementary locking members at 7.1 and 8.1 are arranged on the guiding socket 7 and on the support socket 8. Complementary locking members at 1.2 and 7.2 are arranged on the first connector part 1 and on the guiding socket 7. The wall of the first tubular member is made rigid at 9 in the intermediate portion thereof to facilitate introduction thereof into the second tubular member 5. Possibly occurring breakable membranes are indicated as 10 over the ends of members 2 and 5.

Figure 1B:
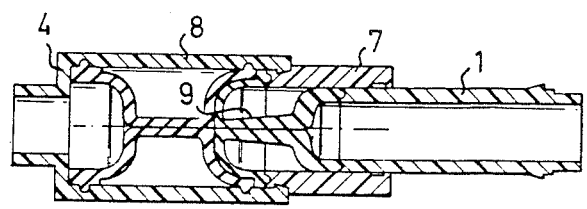
Figure 1C:
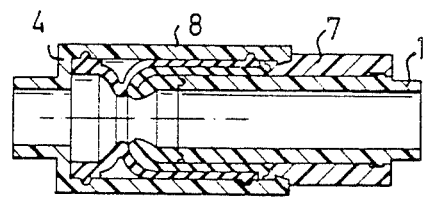

FIG. 1b is similar to FIG. 1c except that parts 1 and 4 are assembled and locking members 7.1 and 8.1 are in locking relationship.

In FIG. 1c the first connector part 1 has been pushed through the guiding socket 7 into the second connector part 4 thus that the first flexible tubular member 2 has been introduced therein and inverted inside out into the second flexible tubular member 5 thus that their sealing surfaces 3 and 6 sealingly bear on each other, and thus that communication is opened between spaces AO and BO. Locking members 1.2 and 7.2 are in locking relationship with each other. Some reference numbers which are the same as in FIG. 1a are omitted in FIGS. 1b and 1c.

The connection device shown in FIG. 2 is rotation symmetrical. With reference to FIGS. 2a and 2b a first connector part 11 is generally tube-shaped. A flexible tubular member 12 is attached at the distal end of part 11, said member 12 having a sealing surface 13 bearing on the outer surface of a cylindrical rod 17 sealing an opening 18 therein to a space A1O, which may be entirely within the rod as shown and may for example contain drug granules, or which has an axial bore through the rod in communication with an adjoining space. A second connector part 14 is generally tube-shaped and has two tubular sockets through the wall thereof, said sockets defining a space B1O as a transversal channel which at each end may continue into a vessel of any kind, e.g. a liquid channel connecting a liquid container and an intravenous needle. A flexible tubular member 15 is attached to part 14 at its proximal end and is closed at its distal end. Member 15 has a sealing surface 16 bearing on an inner surface 19 of the second connector part 14 sealing an opening 20 to space B1O. A rigidifying flange portion 21 of the tubular member 12 has an abutting groove 23 complementary with the end 22 of the second connector part 14.

Figure 2A:
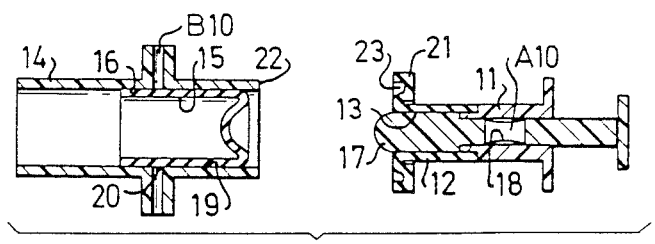
Figure 2B:
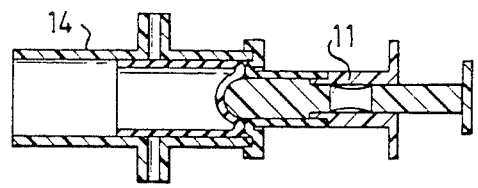
Figure 2C:
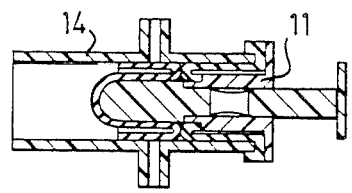
Figure 2D:
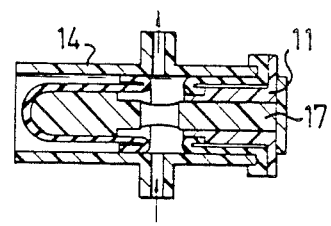

On assembling the connecting device abutment occurs at 22 as shown in FIG. 2b. As shown in FIG. 2c tubular member 12 is then introduced and inverted into the second connector part 14 by pushing the first connector part 11 whereby its sealing surface will sealingly bear on a part of the inner surface 19 of the second connector part 14 between its end 22 and opening 20. Simultaneously tubular member 15 is inverted by the force of rod 17, which is actuated by part 14. A portion of the sealing surface 16 will sealingly bear on the outer surface of the rod 17. On pushing the rod through the first connector part 11 a further portion of member 15 is inverted, opening 20 is uncovered and space A1O is brought in register with opening 20 to communicate with the transversal channel of space B1O as shown in FIG. 2d. Some reference numbers which are the same as in FIG. 2a are omitted in FIGS. 2b, 2c and 2d.

The connection device may, by adapting material, dimensions and abutting and locking members be made releasable, re-sealable and reconnectable, possibly re-using only one of the connector parts (e.g. 4) together with a new other connector part (1). Alternatively, the connection device may be non-releasable.

A flexible material for the tubular members may be a plastic or elastic material e.g. silicon polymer.

I claim:

1. A connection device for establishing communication between first and second spaces in a manner that prevents exposure of the spaces to contamination from the environment and vice versa comprising;
    a first unit adapted to communicate with the first space and including a first connector part, a first tubular member of flexible material having an inner sealing surface adapted to seal the first space from the environment by engaging either itself or a surface of a component of the first unit, and an actuating member movable relative to the first connector part between first and second positions;
    a second unit adapted to communicate with the second space and including a second connector part and a second tubular member of flexible material having a sealing surface adapted to seal the second space from the environment by engaging itself or a surface of a component of the second unit;
    the first and second units being engageable such that a portion of the tubular member of at least one of the units is in sealed relation with a portion of a component of the other unit when the member is in the first position; and
    the actuating member being adapted upon movement from the first to the second position to invert the first tubular member inside out such that the sealing surface thereof is brought into sealing engagement with a surface of the second connector part and also being adapted to move the sealing surface of the second tubular member into sealing engagement with a surface of a component of the first unit, the inversion of the first tubular member and movement of the second tubular member being such as to displace portions thereof that have been exposed to contamination away from portions of the units that have not been exposed to contamination.

2. A connection device according to claim 1, characterized in that the inner sealing surface of the first tubular member has opposite portions which sealingly bear on each other;
    that the sealing surface of the second tubular member has opposite inside portions which sealingly bear on each other;
    and that on joining the units portions of the sealing surfaces of the two tubular members will be brought to sealingly bear on each other.

3. A connection device according to claim 2, characterized in that the first tubular member is connected between the first connector part and the actuator member such as to cause the inversion thereof.

4. A connection device according to claim 1, characterized in that the inner sealing surface of the first tubular member has opposite portions which sealingly bear on the outer surface of an actuating member inside said tubular member, said actuating member being adapted to be inserted into the second connector part, which outer surface has at least one opening into the first space; that the sealing surface of the second tubular member is an outward surface which sealingly bears on the inner surface of a cavity around the second tubular member, which cavity in said inner surface has at least one opening into the second space; and that on joining the units the sealing surface of the first tubular member is brought, on introducing the actuating member into the second connector part, to sealingly bear on the inner surface of the cavity of the second connector part at the same time as the sealing surface of the second tubular member is brought to sealingly bear on the outer surface of the actuating member, whereupon the two openings are uncovered and brought into communication with each other.

5. A connection device according to claim 1, characterized in that either or both sealing surfaces are coated with adhesive material.

6. A connection device according to claim 1, characterized in that the units include means for irreversible connection of the connector parts.

7. A connection device according to claim 1, characterized in that the units are adapted to be disconnected, whereupon the two spaces are resealed from exposure to the environment.

8. A connection device according to claim 1, characterized in that a membrane is arranged to cover the ends of either or both tubular members facing away from the respective spaces.

* * * * *